United States Patent [19]

Pries et al.

[11] Patent Number: 5,408,312
[45] Date of Patent: Apr. 18, 1995

[54] DEVICE FOR THE QUALITATIVE AND/OR QUANTITATIVE DETERMINATION OF THE COMPOSITION OF A SAMPLE THAT IS TO BE ANALYZED

[75] Inventors: Ralph H. Pries, Dortmund; Dae-Jin Yoon, Schwerte; Kim Yoon-Ok, Am Heedbrink, 21,4600 Dortmund, all of Germany

[73] Assignee: Kim Yoon-Ok, Dortmund, Germany

[21] Appl. No.: 30,320
[22] PCT Filed: Sep. 28, 1991
[86] PCT No.: PCT/DE91/00769
    § 371 Date: Oct. 22, 1993
    § 102(e) Date: Oct. 22, 1993
[87] PCT Pub. No.: WO92/06366
    PCT Pub. Date: Apr. 16, 1992

[30] Foreign Application Priority Data
Sep. 28, 1990 [DE] Germany .......... 40 30 836.7

[51] Int. Cl.⁶ .................................................. G01J 1/04
[52] U.S. Cl. .................................. 356/236; 250/228
[58] Field of Search .............. 356/73, 236, 417, 317,
                                       356/318; 250/228

[56] References Cited

U.S. PATENT DOCUMENTS

| | | | |
|---|---|---|---|
| 4,310,246 | 1/1982 | Blazek | 356/236 |
| 4,558,131 | 4/1987 | Stark | 356/236 |
| 4,575,252 | 3/1986 | Akiyama | 356/236 |
| 4,873,430 | 10/1989 | Juliana et al. | 250/228 |
| 4,892,409 | 1/1990 | Smith | 250/228 |
| 4,900,923 | 2/1990 | Gerlinger | 250/228 |
| 5,098,187 | 3/1992 | Judge | 250/228 |
| 5,164,586 | 11/1992 | Hohberg et al. | 250/228 |
| 5,258,363 | 11/1993 | Hed | 356/236 |

FOREIGN PATENT DOCUMENTS

| | | | |
|---|---|---|---|
| 58-171641 | 10/1983 | Japan | 356/236 |
| 59-60229 | 4/1984 | Japan | 356/236 |

Primary Examiner—Robert P. Limanek
Assistant Examiner—Minhloan Tran
Attorney, Agent, or Firm—Antonelli, Terry, Stout & Kraus

[57] ABSTRACT

A device for the qualitative and/or quantitative determination of the composition of a sample to be analyzed. The device includes at least one hollow body which is coated on the inside with an optically reflecting material or is composed completely of an optically reflecting material, and which is provided with at least one aperture. At least one radiation detector is provided proximate to the hollow body in the interior of the hollow body or in the vicinity of the hollow body. At least one ATR (Attenuated Total Reflection) element covers the at least one aperture of the hollow body, and the sample which is to be analyzed is disposed at the side of the ATR element turned away from the hollow body. At least one primary radiation source provides radiation which is received by the ATR element without directly entering the hollow body.

24 Claims, 3 Drawing Sheets

DEVICE FOR THE QUALITATIVE AND/OR QUANTITATIVE DETERMINATION OF THE COMPOSITION OF A SAMPLE THAT IS TO BE ANALYZED

TECHNICAL FIELD

The present invention relates to a device for the qualitative and/or quantative determination of the composition of a sample which is to be analyzed.

STATE OF THE ART

Known are so-called photometer balls which are capable of reflecting on the inside: photometer balls have the job of integrating diffusely reflected radiation of a sample that is to be analyzed and/or of a standard (sample with a known composition). Such photometer balls, also called Ulbricht balls, require primary radiation, which is either beamed into the ball or whose source of radiation is located within the cavity of the ball, respectively inside the wall of the ball, in order to generate diffuse reflection. The reflected part of the radiation regularly reflected by the sample that is to be analyzed has a disturbing effect because it adulterates the measuring signal significantly. Therefore, usually an attempt is made to screen out the regularly reflected radiation (incidence angle= reflection angle) by means of a so-called radiation trap.

In addition to this a reflection method is known which utilizes the physical phenomena accompanying radiation reflection at the interface of two optically differently thick media. This process is known by the names ATR (Attenuated Total Reflection) spectroscopy or FMIR method. The device required to conduct this process contains the so-called ATR element, which, for example, consists of a prism of trapezoidal design. Deposited on the top side and underside of the element is the probe that is to be examined. Due to the trapezoidal cross-section of the ATR element, the parallel beam pencil which hitting the slanted side of the element is totally reflected (usually) several times back and forth inside the element.

Nonetheless, however, some of the electromagnetic energy penetrates the optically thinner medium. As soon as the thinner medium absorbs the radiation that has penetrated, reflection is no longer total. The depth of penetration, for instance, of an infrared radiation depends, i.a., on the selected wavelength and the incidence angle. Following passage of the radiation through the element, the radiation, weakened by the absorbed part thereof, is measured. This process, which works with the "weakened total reflection", has, however, the drawback that it practically permits only, according to the present state of the art, semi-quantative analyses.

DESCRIPTION OF THE INVENTION

The object of the present invention is therefore to provide a device for the determination of the composition of a sample to be analyzed with which both the qualitative and quantitative determination can be conducted with great accuracy. Compared to the state of the art devices, considerably improved are to be primarily analysis and measuring precision as well as detection ability, which is an essential criterium for the assessment of the quality of the analytical method.

The present invention is based on the striking revelation that this goal can be realized by means of a combination of the, as such known, photometer ball and an, as such known, ATR element. Herein the present invention proceeds from the idea to conduct primary radiation to the sample outside the photometer ball as well as from the sample outside the photometer. In this manner only the diffuse radiation coming from the sample reaches the cavity of the photometer ball so that the normally occurring disturbance due to primary radiation is obviated.

In the present invention, therefore, the ATR element or elements are initially utilized, contrary to the present state of the art, only to conduct radiation to the sample that is to be examined.

An element of the invention is, therefore, that in order to be able to integrate diffuse radiation, a device is created which is provided with at least one hollow body capable of reflecting from its interior and having at least one aperture which is covered by an ATR element. The sample to be analyzed is disposed on the underside of the ATR element or elements (FIGS. 1 and 2), respectively on the side turned away from the hollow body.

Furthermore, (at least) one source of primary radiation, whose radiation is directed at one of the sides of the sample not covered by the ATR element or elements and at least one radiation detector are provided in the area of the hollow body. This detector registers the diffuse radiation emitted from the sample through the ATR element inside the hollow body and/or is reflected in the hollow body.

In other words, the primary radiation is first conducted into the ATR element. The reflected radiation leaves the ATR element at the opposite end of the element following single or multiple total reflection at the interfaces of the optically differently thick media, i.e. the interfaces of the sample and the ATR element, with the total reflection being weakened due to absorption in the optically thinner medium. The diffusely reflected, respectively under certain conditions desired fluorescent radiation, from the sample penetrates the ATR element passing through the aperture of the hollow body into the interior thereof and encounters the radiation detector there, if need be, following single or multiple reflection at the inner wall of the hollow body in such a manner that the detector registers it.

This way only diffuse, respectively fluorescent radiation, enters the hollow body. By this means the measurement interfering radiation background caused by the primary radiation in the present state of the art is considerably reduced.

The diffuse radiation registered by the radiation detector, respectively, light detector, permits making both a qualitative and a quantative statement on the composition of the sample to be examined with an accuracy that is distinctly above the accuracy achieveable with conventional devices.

The invented device working with diffuse reflection essentially improves not only the known process but also substantially increases the advantages of the state of art ATR method. Moreover, the invented device, a combination of an, as such known, photometer ball and a ATR element, is also suited for detecting the fluorescent radiation generated in the sample. For this purpose, if need be, appropriate measures such as suited stimulating light sources and filters are to be provided.

The hollow body may be designed as a polyhedron, (rotation) ellipsoid, paraboloid, hemisphere, ball or as an irregular body. Decisive is only that the hollow body has integrating properties which can be realized well in certain cases due to an irregular shape.

In order to optimize measurement accuracy, the aperture of the hollow body covered by the ATR element should only make up a small part of the inner surface. In particular, the area of the aperture should not make up more than 10% of the entire interior surface of the hollow body and preferably not more than 5%. In this manner, measurement inaccuracies occurring, in particular, because the radiation from inside the hollow body reflected back again to the opening is minimized.

The hollow body or bodies, as previously explained, may have a great variety of different shapes and sizes. In particular, a device may also be provided with several hollow bodies having different shapes and sizes. The maximum diameter of the hollow body should, however, not exceed 1000 mm. Preferable, however, are dimensions of less than 200 mm and, in particular, between 2 mm and 0.20 mm.

The radiation detector or detectors for registration of the diffuse radiation from the sample may be disposed in a great variety of different ways. The radiation detectors may be arranged in a second wall aperture of the hollow body; just as the radiation detector or detectors may also be positioned inside the hollow body. Due to the fact that in accordance with the present invention the reflection of a part of the primary radiation is prevented inside the hollow body, an element of the invention is that the significance of the disposition of the radiation detector in the area of the hollow body only plays a subordinate role.

In interest of as high as possible measurement accuracy, it is a matter of course that the ATR element should cover the corresponding aperture of the hollow body as tightly as possible. For this purpose, there are various sealing possibilities available, for example, caskets or flanges.

The shape of the ATR element may vary, for example, it may be semi-cylindrical or prismatic. From the resulting conduction of radiation inside the ATR element, for example due to the special prismatic shape, the number of total reflections can be increased. In this manner the probability of interaction between the sample and the radiation conducted to it is increased, resulting in an more material-specific signal. The number of reflections is proportional to the effective length of the path of the radiation inside the element and to the cotangent of the incidence angle and inversely proportional to the thickness of the element.

A preferred embodiment is a dovetail prism the size of which depends on the desired number of reflections and on the size of the integrating hollow body utilized and is yielded by the previously mentioned dimensioning of the corresponding aperture in the wall of the hollow body. The thickness should be greater than 0.25 mm and the effective length (central point of the entrance aperture to central point of the exit aperture) less than 100 mm. For specific applications, an ATR element in the shape of an (if need be, modified) hemisphere is particularly preferred.

The hollow body may be composed of a material having great reflection capability such as a metal or a ceramic material; likewise, for example, the interior surface of a metal wall may be provided with a ceramic coating, for example of magnesite, or with an appropriate other coating. The thickness of the wall of the integration body should as a rule not exceed 70 mm.

The described source of radiation may, for example, be provided with an xenon vapor lamp or a heated ceramic material. However, it may also be designed as a radiation source emitting a highly coherent laser radiation. In this event, it is advantageous to conduct the collimated radiation directly, if need be, via a suited lightwave conductor, from the radiation source to the entrance surface of the element.

The invented combined device permits realization of various analytical measurement of a great variety of different substances. Solid, liquid, and even gaseous substances can be examined. The composition of the various substances can be determined qualitatively as well as quantitatively. By way of illustration, the invented combined device can be utilized to analyze drinking and waste water, exhaust fumes, foods, etc. as well as for chemical determination of both biological and biochemical materials. The invented device is also suited for examining surface impurities on various materials. In particular, the invented combined device will be utilized in analysis in clinical-chemical areas. On the other hand, the device can also be used in other atomic and molecular spectroscopic processes. Finally, it must be mentioned that the invented device also permits destruction-free analysis. The sample itself is deposited on the underside (FIGS. 1 and 2) of the ATR element, in the case of liquid substances the appropriate surface is moistened with the liquid, respectively pressed against the solid sample.

Further features of the present invention are yielded by the features of the subclaims and the other application documents.

A BRIEF DESCRIPTION OF THE DRAWING

The present invention is made more apparent in the following using a preferred embodiment. The strongly schematic representation shows in:

FIG. 1. a longitudinal section through an invented device,

FIG. 2. a cross-section through the device according to FIG. 1,

FIG. 3. a top view from below of the device according to FIG. 1.

DESCRIPTION OF A PREFERRED EMBODIMENT

Figure 1:
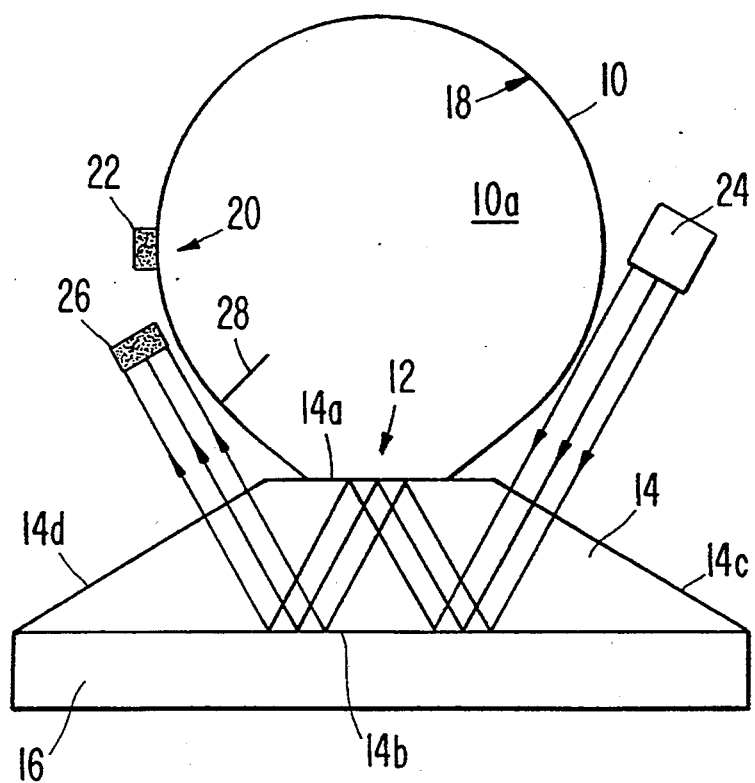
Figure 2:
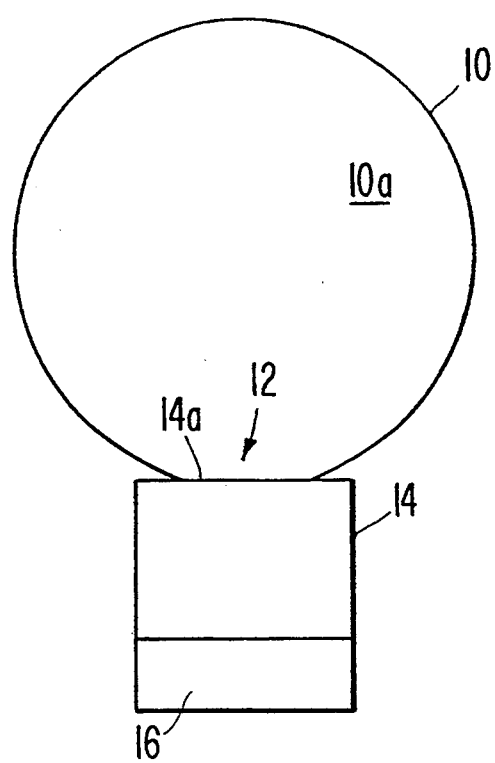
Figure 3:
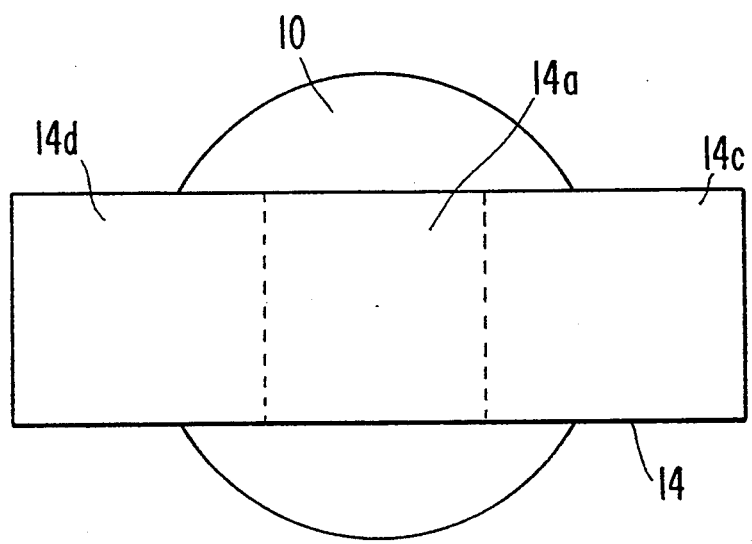

The device according to FIG. 1 is composed of a, in the illustrated preferred embodiment, hollow body 10 designed as a ball, which on its underside is provided with an aperture 12 which is completely covered by the surface 14a of an ATR element 14. Element 14 is designed as a dovetail-shaped prism and has accordingly an underside 14b and two slanted lateral surfaces 14c, respectively 14d.

Disposed on the underside 14b is a sample 16 to be analyzed, which, for example, is composed of a synthetic material with impurities on its surface.

The ball 10 is composed of a metal wall which is provided with a reflecting coating 18 on the interior side.

In the left section of the ball 10 of FIG. 1 there is a further aperture 20 in which a radiation detector 22 is disposed.

Into the interior 10a of the ball 10 extends a plate 28 which is also provided with a reflecting coating and is attached to the interior wall (coating) 18 of the ball 10 covering the direct beam path between the aperture 12 and the radiation detector aperture 20.

Via a radiation source, schematically depicted with the reference number 24, emitting highly coherent laser radiation, the primary radiation is conducted via the lateral surface 14c into the element 14.

Between the primary radiation source 24 and the ATR element 14 (respectively between the ATR element and the radiation detector 26) optically suited separation devices, such as, e.g., lenses (combinations), shutters, filters, etc., can be inserted in order to optimize the optical quality of the image. One or more filters can also be located between hollow body 10 and ATR element 14. For reasons of clarity, however, the figure does not show such optical separation elements. Moreover, the ATR element 14 and the other optical separation elements may also be coated in a suited manner, in order to achieve certain properties, respectively to filter out undesired wavelengths.

The parallel beam pencil is practically totally reflected at the underside 14b until it reaches the top side 14a from where it is reflected (practically) totally analogously back. This back and forth reflection is repeated more or less often depending on the selected incidence angle of the primary radiation and on the dimensions of the crystal. The beam path is again only schematically depicted in the figure for reasons of clarity. Finally the totally reflected primary radiation exits via the opposite lateral surface 14d of the element 14.

A part of the primary radiation, however, penetrates the sample 16 and is (later) reflected from there diffusely. This diffusely reflected radiation reaches the ATR element 14 and enters, if it does not go beyond the limiting angle of the total reflection, through the top side 14a into the interior 10a of the ball 10, is reflected back and forth on the interior wall 18 in accordance with the principles of geometric optics until it leaves the ball via the aperture 20, encounters the radiation detector 22 and is registered by the same. The path of the diffuse radiation is not depicted for reasons of clarity.

The measurement of the diffuse radiation via the radiation detector 22 permits both a quantitative as well as a qualitative determination of radiation absorbed by the sample, respectively the scattered radiation, and therefore a respective analysis of the sample to be examined. Diffuse radiation is proportional to the absorbtion ability of the sample and is reversely proportionally to its ability to scatter. The weakened primary radiation leaving the element 14 through the surface 14d is registered with the aid of an additional radiation detector 26 disposed at the beam-exit-side end of the ATR element. In other words: in accordance with the concept of the present invention, first only the radiation diffusely reflected by the sample which reaches the interior of the integrating hollow body through the ATR element is measured. The ATR element is utilized, as already mentioned, to conduct the radiation to the to-be-examined sample. Thus initially the aim was not measurement of the weakened primary radiation leaving the ATR element. The present invention, however, was conceived from the beginning in such a manner that it can also measure the primary radiation, in addition, in order to increase the reliability of the correctness of the analyses results. This means that a sample can be examined simultaneously with two independent methods of analysis (respectively even three, if, if desired, the fluorescent radiation emitted from a sample is registered with the aid of additional integration hollow bodies and radiation detectors). If both (respectively all three) yield the same results, the correctness of the analysis is additionally substantiated.

What is claimed is:

1. A device for the qualitative and/or quantitative determination of the composition of a sample to be analyzed, comprising:
    at least one hollow body which is one of coated on the inside with an optically reflecting material and composed completely of an optically reflecting material, and which is provided with at least one aperture, and at least one radiation detector provided proximate to said hollow body,
    at least one ATR (Attenuated Total Reflection) element covering said at least one aperture of said hollow body,
    at the side turned away from said hollow body of said ATR element, the sample which is to be analyzed can be disposed, and
    the radiation of at least one primary radiation source being received by said ATR element without directly entering said hollow body.

2. A device according to claim 1, characterized by said hollow body having the shape of one of a polyhedron, ellipsoid, paraboloid, a hemisphere, a ball, a regular body, and an irregular form.

3. A device according to claim 2, characterized by said shape of said hollow body being one of a form of a regular body.

4. A device according to one of the claims 1 to 3, characterized by the entire area of said at least one aperture of said hollow body amount to maximumly 10% of the interior surface of said hollow body.

5. A device according to claim 4, characterized by said entire area of said at least one aperture of said hollow body amount to maximumly 5% of said interior surface of said hollow body.

6. A device according to claim 1, characterized by the direct beam path between the at least one aperture and the radiation detector being interrupted by at least one body.

7. A device according to claim 1, characterized by said ATR element having the shape of one of a prism, a semicylinder, a trapezoid, a hemisphere, a regular body, and an irregular form.

8. A device according to claim 7, characterized by the shape of said ATR element being a form of a regular body.

9. A device according to claim 1, characterized by at least one optical filter being disposed between said hollow body and said ATR element.

10. A device according to claim 1, characterized by the surface of said ATR element being one of completely and partially optically refined.

11. A device according to claim 1, characterized by said primary radiation source being Xe an Xe vapor lamp, a Hg high-pressure lamp, and a heatable ceramic.

12. A device according to claim 11, characterized by said ceramic being one of an oxide and carbide ceramic.

13. A device according to claim 1, characterized by said primary radiation source being a laser.

14. A device according to claim 1, characterized by said primary radiation source being connected to said ATR element via a lightwave conductor.

15. A device according to claim 1, characterized by at least one further radiation detector being provided in the outer region of said ATR element for the detection of weakened primary radiation leaving said ATR element through its lateral surface.

16. A device according to claim 15, characterized by said further radiation detector being connected via said lightwave conductor to said ATR element.

17. A device according to claim 1, characterized by the largest dimension of all the parts required for said device being maximumly 1000 mm.

18. A device according to claim 17, characterized by said hollow body, said primary radiation source and said radiation detector being no larger than 20 mm in its greatest dimension.

19. A device according to claim 1, characterized by said primary radiation source and said radiation detector being no larger than 2 mm in its greatest dimension.

20. A device according to claim 1, characterized by between at least one of said hollow body and said ATR element, said primary radiation source and said ATR element, and said ATR element and said radiation detector, being arranged an optical separation device along a beam path.

21. A device according to claim 1, characterized by an incidence angle of said primary radiation onto said ATR element being adjustable.

22. A device according to claim 21, characterized by said incidence angle being selected in such a manner that said sample generates fluorescent radiation.

23. A device according to claim 1, characterized by said primary radiation source emitting radiation of varying wavelengths which can be conducted into said ATR element one of separately and mixed.

24. A device according to claim 1, characterized by electric signals applied at said radiation detector being usable for at least one of multi-element and multiple-component analysis by means of at least one frequency filtering processes.

* * * * *